United States Patent [19]

Patel

[11] Patent Number: 5,705,721
[45] Date of Patent: Jan. 6, 1998

[54] DISPERSANT FOR CHLOROPRENE UNIT FOULING

[75] Inventor: Natu R. Patel, Houston, Tex.

[73] Assignee: Nalco Chemical Company, Naperville, Ill.

[21] Appl. No.: 743,016

[22] Filed: Nov. 1, 1996

Related U.S. Application Data

[63] Continuation-in-part of Ser. No. 588,646, Jan. 19, 1996, abandoned.

[51] Int. Cl.$^6$ ................................................. C07C 17/38
[52] U.S. Cl. .................................................... 570/238
[58] Field of Search ............................................. 570/238

[56] References Cited

U.S. PATENT DOCUMENTS

| | | |
|---|---|---|
| 2,182,178 | 5/1939 | Pinkernelle . |
| 2,490,744 | 12/1949 | Trigg et al. . |
| 3,172,892 | 3/1965 | LeSuer et al. . |
| 3,219,666 | 11/1965 | Norman et al. . |
| 3,235,484 | 2/1966 | Colier . |
| 4,883,886 | 11/1989 | Juang . |
| 5,171,420 | 12/1992 | Forester . |
| 5,171,421 | 12/1992 | Forester . |

FOREIGN PATENT DOCUMENTS

| | | |
|---|---|---|
| 599931 | 6/1960 | Canada . |

*Primary Examiner*—Alan Siegel
*Attorney, Agent, or Firm*—Robert A. Miller; Kelly L. Cummings

[57] ABSTRACT

The present invention provides a method for inhibiting fouling deposits in chloroprene production units. The deposits are inhibited by addition to the chloroprene feedstock of an effective amount of a dispersant prepared in accordance with this invention. The dispersants comprise imides which are prepared by reacting substituted succinic anhydrides with amines.

19 Claims, No Drawings

DISPERSANT FOR CHLOROPRENE UNIT FOULING

The present application is a continuation-in-part of application Ser. No. 08/588,646, filed Jan. 19, 1996 now abandoned by Natu R. Patel entitled "Dispersant for Chloroprene Unit Fouling", the disclosure of which is incorporated herein by reference.

FIELD OF THE INVENTION

The present invention is a method for inhibiting fouling deposits in chloroprene production units. The deposits are inhibited by addition to the chloroprene feedstock of an effective amount of a dispersant prepared in accordance with this invention. The dispersants comprise imides which are prepared by reacting substituted succinic anhydrides with amines.

BACKGROUND OF THE INVENTION

Unsaturated and chlorinated hydrocarbons are generally manufactured by high temperature processes which require either cracking or further chlorination and, in some cases, hydrochlorination of unsaturated compounds. An important commercial product in the class of chlorinated and unsaturated hydrocarbons is chloroprene.

Chloroprene is currently produced from butadiene. There are three steps in the conversion of butadiene to chloroprene. First, chlorination; second, isomerization; and finally, caustic dehydrochlorination are required to obtain the desired product. Vapor-phase chlorination, in a free radical mechanism, is the method of choice for chlorination. Critical to the success of this procedure are the adequate mixing of gas streams to prevent over-chlorination, avoidance of condensed phases in which the product can be chlorinated in preference to the diene and completion of the chlorination to avoid by-product formation in the refining operation. The preferred temperature range for commercial operation is from 290°–330° C.

The crude chlorination products are condensed from the excess butadiene which is then recycled to the reactor. Systems for refining the crude product vary considerably, depending on the degree of integration with subsequent isomerization and dehydrochlorination steps. Among the impurities which must be removed from the desired chloroprene product are: 1) low boiling impurities, namely 1- and 2-chlorobutadiene; 2) 1-4-dichloro-2-butene; and 3) higher boiling by-products including trichlorobutene, tetrachlorobutanes, telomers and tars.

One of the major problems encountered during chloroprene processing is fouling. The term fouling as used herein refers to the formation of deposits on the metal surfaces of processing equipment. Fouling deposits most frequently occur at elevated temperatures and vary in composition as to organic, inorganic or mixed organic and inorganic deposits. The organic deposits are primarily impurities as stated above. Inorganic deposits may contain silica, iron oxide, alkaline earth metal oxides and various metal salts. Inorganic portions may result from corrosion products from the metal surfaces that the process stream contacts, and contaminants from metallic catalysts used in processing.

The efficiency of processing equipment is materially decreased when fouling occurs. The direct results of fouling appear in the form of heat transfer loss, increased pressure drop between the heat exchanger equipment inlet and outlet, and loss in throughput. When fouling deposits accumulate, the equipment must be disassembled and mechanically and chemically cleaned to remove the deposits. Moreover, sometimes both mechanical and chemical cleaning are necessary. In extreme cases of fouling, the equipment must be completely replaced. Consequently, the processing units must be shut down, resulting in lost production.

As there are no effective dispersants for chloroprene production units, a compound which could be added to the unit to prevent fouling would be advantageous over the current solution to the problem, which is the physical removal of foulants. Accordingly, this invention is a method by which a dispersant imide may be added to inhibit fouling in situ.

The preparation of polyisobutylene succinimides has been disclosed in U.S. Pat. No. 3,172,892. Such compounds have been disclosed as anti-foulants for crude oils, as in U.S. Pat. No. 3,235,484. Imides further reacted with maleic anhydride have been disclosed as crude oil anti-foulants in U.S. Pat. No. 5,171,421. A mixture of a polyalkylene succinimide along with other compounds was disclosed as a crude oil anti-foulant in U.S. Pat. No. 5,171,420. However, none of these references disclose solutions to the specific problems posed by foulants produced when butadiene is converted to chloroprene and/or recovered from the process stream.

SUMMARY OF THE INVENTION

The present invention is a method for inhibiting fouling deposits in chloroprene production units. The deposits are inhibited by addition to the chloroprene feedstock of an effective amount of a dispersant prepared in accordance with this invention. The dispersants comprise imides which are prepared by reacting substituted succinic anhydrides with amines.

DESCRIPTION OF THE INVENTION

The invention is a method of inhibiting the formation of foulant deposits on the surfaces of processing equipment in contact with a chloroprene process stream during chloroprene recovery which comprises adding to the liquid or gaseous phases of said stream an effective antifouling amount of a dispersant which is a polyalkenylsuccinimide having the formula:

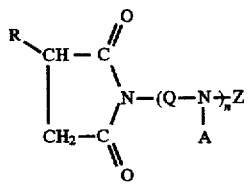

wherein R is an aliphatic alkenyl or alkyl moiety having at least about 50 carbon atoms and less than about 200 carbon atoms, Q is a divalent aliphatic radical, n is a positive integer, A is hydrocarbyl, hydroxyalkyl or hydrogen, Z is H or

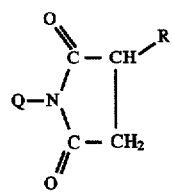

The dispersant may be added in from about 10 to about 20,000 ppm by weight. Preferably, the dispersant is added in from about 50 to about 10,000 ppm by weight. Most preferably, the dispersant is added in from about 100 to about 1,000 ppm by weight. The dispersant may be dissolved in a hydrocarbon solvent prior to addition to the chloroprene process stream. Useful hydrocarbon solvents include toluene, xylene and heavy aromatic naphtha.

The invention is also a method utilizing a dispersant wherein R comprises more than 50 carbon atoms and is a polyalkenyl moiety and Z is

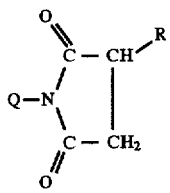

The dispersant may be the reaction product of two equivalents of polyisobutylene succinic anhydride and one equivalent of polyethylene amine. R may comprise a repeated isobutenyl moiety. Preferably, Q is chosen from $C_1$–$C_5$ alkylene and A is hydrogen. The invention is also a method wherein the dispersant has Q as ethylene. R may have a molecular weight of about 1300.

The term recovery, as used herein, refers to processes during chloroprene production subsequent to chlorination. This includes the separation by distillation of unwanted by products. Any equipment utilized for chloroprene recovery is made of glass or highly inert corrosion-resistant metals.

Polyalkenylsuccinic acid or the corresponding polyalkenylsuccinic anhydride compound are well known. They may be purchased from a number of suppliers, with the preferred polyisobutenylsuccinic anhydride sold by Texaco under the trademark TLA-627. This particular compound is a polyisobutenylsuccinic anhydride (PIBSA) having the structure

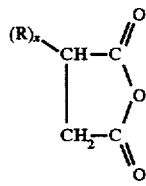

wherein, in this case, R is an isobutenyl repeat unit. The average molecular weight of the polyisobutene used to produce the PIBSA is about 1300.

The preferred polyalkenylsuccinic anhydride (PIBSA) may also be prepared as reported in U.S. Pat. No. 3,235,484 (Colfer), incorporated herein by reference or, more preferably, by the methods reported in U.S. Pat. No. 4,883,886 (Huang) also incorporated by reference herein. As to the Colfer method, the anhydride may be prepared by reaction of maleic anhydride with a high molecular weight olefin or a chlorinated high molecular weight olefin. In the preferred Huang method, reaction of a polymer of a $C_2$–$C_8$ olefin and maleic anhydride are carried out in the presence of a tar and side-product suppressing agent.

The most commonly used sources for forming the aliphatic R substituent on the succinic anhydride compound are the polyolefins, such as polyethylene, polypropylene, polyisobutene, polyamylene, polyisohexylene, etc. The most particularly preferred polyolefin (and the one used to manufacture the preferred polyisobutenylsuccinic anhydride—PIBSA—from Texaco) is polyisobutene. As Golfer states, particular preference is made for such a polyisobutene containing at least about 50 carbon atoms, preferably from at least 60 carbon atoms and most desirably from about 100 to about 130 carbon atoms. Accordingly, an operable carbon atom number range for R is from about 30–200 carbon atoms.

Although the Polyalkenylsuccinic anhydride compounds are preferred, similar succinic acid compounds may also be employed.

Processes for preparing polyalkenylsuccinimide compounds are reported, for instance, in U.S. Pat Nos. 3,219,666; 3,172,892; 2,182,178; and 2,490,744, as well as in the aforementioned Colfer patent. These compounds are prepared via reaction of a hydrocarbyl succinic anhydride, acid or ester with an amine. Again, the hydrocarbyl substituent is normally derived from a polyolefin, such as polypropylene or polyisobutylene containing from 12 to about 200 carbon atoms. The most preferred hydrocarbyl subsitutents are derived from polyisobutylene containing about 50–200 carbon atoms (mol. wt. about 700–2800).

Preferably the polyalkenylsuccinic anhydride or acid is reacted with a polyamine having the structure

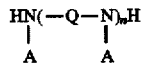

in which n is an integer, A is chosen from hydrocarbyl, hydroxyalkyl or hydrogen with the proviso that at least one A is hydrogen. Q signifies a divalent aliphatic radical. As Colfer indicates, the A substituents can be considered as forming a divalent alkylene radical, thus resulting in a cyclic structure. Q generally, however, is a $C_1$–$C_5$ alkylene, such as ethylene, trimethylene, tetramethylene, etc. Q is most preferably ethylene.

Accordingly, exemplary amines may comprise ethylenediamine, triethylenetetramine, diethylenetriamine, trimethylenediamine, bis(trimethylene)triamine, tris(trimethylene)tetramine tris(hexamethylene)tetramine, decamethylenediamine, N-octyl trimethylenediamine, N,N'-dioctyltrimethylenediamine, N(2-hydroxyethyl) ethylenediamine, piperazine, 1-(2-aminopropyl)piperazine, 1,4-bis(2-aminoethyl)piperazine, 1-(2-hydroxyethyl) piperazine, bis(hydroxypropyl) substituted tetraethylenepentamine, N-3-(hydroxypropyl) tetramethylenediamine, pyrimidine, 2-methylimidazoline, polymerized ethyleneimine, and 1,3-bis(2-aminoethyl) imidazoline.

The reaction of the polyalkyenylsuccinic anhydride with amine to form polyalkenylsuccinimide is conducted at a temperature in excess of 80° C. with use of a solvent, such as benzene, zylene, toluene, naphtha, mineral oil, n-hexane, etc. Preferably, the reaction is conducted at from 100°–250° C. with a molar ratio of precursor anhydride:amine being from about 1:5 to about 5:1, a molar ratio of 1–3:1 preferred.

Another group of amines suitable for use are branched polyalkylene polyamines. The branched polyalkylene polyamines are polyalkylene polyamines wherein the branched group is a side chain containing on the average at least one nitrogen-bonded aminoalkylene, i.e.,

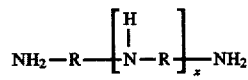

group per nine amino units present on the main chain, for examples, 1–4 of such branched chains per nine units on the main chain, but preferably one side chain unit per nine main chain units. Thus, these polyamines contain at least three primary amino groups and at least one tertiary amino group.

These reagents may be expressed by the formula

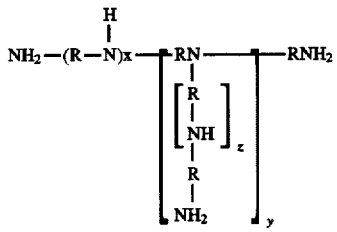

wherein R is an alkylene group such as ethylene, propylene, butylene and other homologues (both straight chained and branched), etc., but preferably ethylene; and x, y and z are integers, x being for example, from 4 to 24 or more but preferably 6 to 18, y being for example 1 to 6 or more but preferably 1 to 3, and z being for example 0–6 but preferably 0–1. The x and y units may be sequential, alternative, orderly or randomly distributed.

The preferred class of such polyamines includes those of the formula

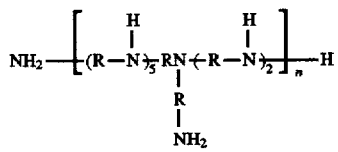

wherein n is an integer, for example, 1–20 or more but preferably 1–3, wherein R is preferably ethylene, but may be propylene, butylene, etc. (straight chained or branched).

The preferred embodiments are presented by the following formula:

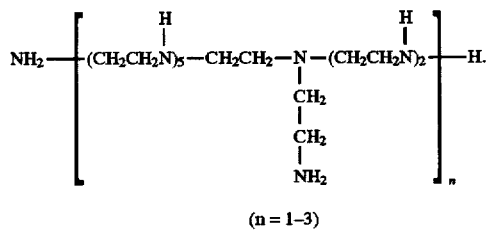

(n = 1–3)

The radicals in the brackets may be joined in a head-to-head or a head-to-tail fashion.

The invention is also a method of inhibiting the formation of foulant deposits on the surfaces of processing equipment in contact with a chloroprene process stream during chloroprene recovery which comprises adding to the liquid or gaseous phases of said stream an effective antifouling amount of a dispersant which is a polyalkenylsuccinimide having the formula:

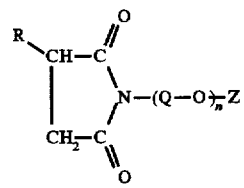

wherein R is an aliphatic alkenyl or alkyl moiety having at least about 50 carbon atoms and less than about 200 carbon atoms, Q is a divalent aliphatic radical, n is a positive integer, A is hydrocarbyl, hydroxyalkyl or hydrogen, Z is H or

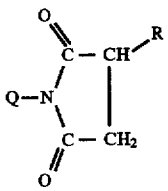

The dispersant may be added in from about 10 to about 20,000 ppm by weight. Preferably, the dispersant is added in from about 50 to about 10,000 ppm by weight. Most preferably the dispersant is added in from about 100 to about 1,000 ppm by weight. The dispersant may be dissolved in a hydrocarbon solvent prior to addition to the chloroprene process stream.

The invention is also a method wherein R comprises more than 50 carbon atoms and is a polyalkenyl moiety and Z is

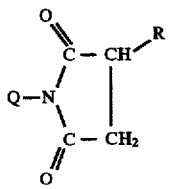

R may comprise a repeated isobutenyl moiety. Preferably, Q is ethylene. R may have a molecular weight of about 1300. The dispersant may be the reaction product of two equivalents of polyisobutylene succinic anhydride and one equivalent of polyoxyalkylene polyamine.

Suitable amines also include polyoxyalkylene polyamines, e.g., polyoxyalkylene amines and polyoxyalkylene triamines, having average molecular weights ranging from about 200 to 4000 and preferably from about 400 to 2000. Illustrative examples of these polyoxyalkylene polyamines may be characterized by the formulae:

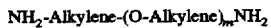

where m has a value of about 3 to 70 and preferably about 10 to 35.

where n is such that the total value is from about 1 to 40 with the proviso that the sum of all of the n's is from about 3 to about 70 and generally from about 6 to about 35 and R is a polyvalent saturated hydrocarbon radical of up to ten carbon atoms having a valence of 3 to 6. The alkylene groups may be straight or branched chains and contain from 1 to 7 carbon atoms, and usually from 1 to 4 carbon atoms. The various alkylene groups present may be the same or different.

More specific examples of these polyamines include:

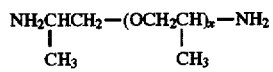

wherein x has a value of from about 3 to 70 and preferably from about 10 to 35 and

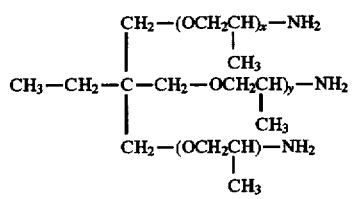

wherein x+y+z have a total value ranging from about 3 to 30 and preferably from about 5 to 10.

The preferred polyoxyalkylene polyamines for purposes of this invention include the polyoxyethylene and polyoxypropylene diamines and the polyoxypropylene triamines having average molecular weights ranging from about 200 to 2000. The polyoxyalkylene polyamines are commercially available.

The dispersant is typically added to a continuous process stream at a point of relatively low pressure to achieve a desired equilibrium concentration throughout the process. In processes in which gaseous and liquid reactants, products and/or solvents are heated or cooled, such as in recovery operations for recycle and reuse. The present dispersant is preferably added upstream of the heat exchangers or coolers to be protected. In the chloroprene production unit, the dispersant is injected as a solution in a hydrocarbon solvent, in line from the reactor vessel to the reboiler. The polyisobutenyl succinimide can be the sole dispersant or may be admixed with other compounds.

The present dispersant may be used as a continuous additive in the hydrocarbon stream, or it can be added periodically to facilitate byproduct removal from the process equipment.

Dispersion of foulants occurs by admixing an effective amount of the polyisobutenyl succinimide in the chloroprene processing stream. Dispersions may be achieved at a stream temperature as low as about −10° C. up to about 500° C. but preferably from about 0° C. to about 400° C.

The following examples are presented to describe preferred embodiments and utilities of the invention and are not meant to limit the invention unless otherwise stated in the claims appended hereto.

EXAMPLE 1

The polyisobutylene succinimide was synthesized from polyisobutylene succinic anhydride and polyethylene polyamine in the following manner. Polyisobutylene succinic anhydride (2 equivalents, supplied by Texaco) and heavy aromatic naphtha solvent were placed in a three neck round bottom flask equipped with a stir bar, temperature controller, Dean-Stark trap and a condensor. Subsequently, polyethylene polyamine (1 equivalent, supplied by Union Carbide) was added. The reaction mixture was heated to approximately 140° C. for 1.5 hours and the water formed during the reaction was collected into the Dean-Stark trap. IR spectroscopy confirmed the presence of product. The imide thus formed will hereinafter be refered to as Example 1.

EXAMPLE 2

A sample of a stream containing foulants from a chloroprene production unit was filtered by vacuum filtration to remove foulant from the stream. This process resulted in the collection of two types of foulants: a thick liquid and a black gummy residue.

The thick liquid was not soluble in hexane or in a 1:1 mixture of hexane and dichloromethane. However, the liquid was soluble in 1-methyl-2 pyrrolidinone (NMP), so this solvent was selected for test purposes.

To evaluate the dispersant of the invention, an aliquot of a 5% solution of the dispersant to be tested was dissolved in 10 ml of dichloromethane. Next, a solution of foulant was made by dissolving 5 g of the black gummy residue in 10 mL of NMP. A 100 uL aliquot of foulant solution was then added to the dispersant-containing solution and shaken vigorously for 60 seconds. The mixture was then allowed to stand for 2 hours at room temperature.

After the mixture had been allowed to settle, the volume of any solid material at the bottom of the tube was measured and compared to the volume of the settled material in a control sample of a stock solution containing no dispersant.

Percent dispersion for each test is presented as the percent difference of the volume of the non-dispersed material. The imide of this invention was compared against a surfactant with some dispersing capabilities. Results indicate excellent dispersant activity for the polyisobutylene anhydride/polyethylene amine reaction product in chloroprene production streams. At higher concentrations, the polyisobutylene succinic anhydride/polyethyleneamine reaction product causes complete dispersion.

TABLE I

| Treatment | Dispersant (μl) | Solids Observed (ml) | % dispersed |
|---|---|---|---|
| None | 0 | 0.9 | 0 |
| Compound A | 50 | 0.25 | 72.3 |
|  | 75 | 0.15 | 83.4 |
|  | 100 | 0.10 | 88.9 |
| Example 1 | 50 | 0.01 | 98.9 |
|  | 75 | 0.0 | 100.0 |
|  | 100 | 0.0 | 100.0 |

Compound A = Surfactant Corexit 314, an amide/ester mixture commercially available from Exxon.

EXAMPLE 3

Polyisobutylene succinimide was tested for dispersant activity against both types of foulants which can occur in a chloroprene production unit. Test mixtures in ratios of from 1:1 to 3:1 of black residue to thick liquid were formulated as in Example 2. The procedure of Example 2 was utilized to test the dispersing capabilities of Example 1. Test results were similar to those enumerated in Table 1, indicating that the imide was as effective against the combination of black residue and thick liquid as against the thick liquid alone.

Changes can be made in the composition, operation and arrangement of the method of the present invention described herein without departing from the concept and scope of the invention as defined in the following claims:

I claim:

1. A method of inhibiting the formation of foulant deposits on the surfaces of processing equipment in contact with a chloroprene process stream during chloroprene recovery which comprises adding to the liquid or gaseous phases of said stream an effective antifouling amount of a dispersant which is a polyalkenylsuccinimide having the formula:

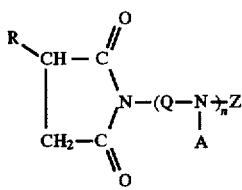

wherein R is an aliphatic alkenyl or alkyl moiety having at least about 50 carbon atoms and less than about 200 carbon atoms, Q is a divalent aliphatic radical, n is a positive integer, A is hydrocarbyl, hydroxyalkyl or hydrogen, Z is H or

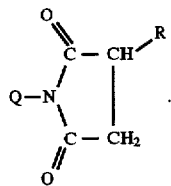

2. The method of claim 1 wherein the dispersant is added in from about 10 to about 20,000 ppm by weight.

3. The method of claim 1 wherein the dispersant is added in from about 50 to about 10,000 ppm by weight.

4. The method of claim 1 wherein the dispersant is added in from about 100 to about 1,000 ppm by weight.

5. The method of claim 1 wherein the dispersant is dissolved in a hydrocarbon solvent prior to addition to the chloroprene process stream.

6. The method of claim 1 wherein R comprises more than 50 carbon atoms and is a polyalkenyl moiety and Z is

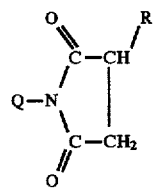

7. The method of claim 6 wherein R comprises a repeated isobutenyl moiety.

8. The method of claim 7 wherein Q is chosen from $C_1$–$C_5$ alkylene and A is hydrogen.

9. The method of claim 8 wherein Q is ethylene.

10. The method of claim 9 wherein R has a molecular weight of about 1300.

11. A method of inhibiting the formation of foulant deposits on the surfaces of processing equipment in contact with a chloroprene process stream during chloroprene recovery which comprises adding to the liquid or gaseous phases of said stream an effective antifouling amount of a dispersant which is a polyalkenylsuccinimide having the formula:

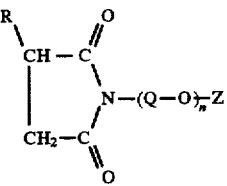

wherein R is an aliphatic alkenyl or alkyl moiety having at least about 50 carbon atoms and less than about 200 carbon atoms, Q is a divalent aliphatic radical, n is a positive integer, A is hydrocarbyl, hydroxyalkyl or hydrogen, Z is H or

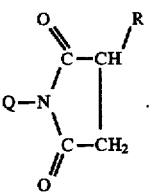

12. The method of claim 11 wherein the dispersant is added in from about 10 to about 20,000 ppm by weight.

13. The method of claim 11 wherein the dispersant is added in from about 50 to about 10,000 ppm by weight.

14. The method of claim 11 wherein the dispersant is added in from about 100 to about 1,000 ppm by weight.

15. The method of claim 11 wherein the dispersant is dissolved in a hydrocarbon solvent prior to addition to the chloroprene process stream.

16. The method of claim 11 wherein R comprises more than 50 carbon atoms and is a polyalkenyl moiety and Z is

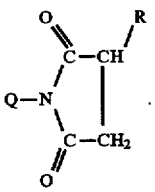

17. The method of claim 16 wherein R comprises a repeated isobutenyl moiety.

18. The method of claim 17 wherein Q is ethylene.

19. The method of claim 18 wherein R has a molecular weight of about 1300.

* * * * *

UNITED STATES PATENT AND TRADEMARK OFFICE
CERTIFICATE OF CORRECTION

PATENT NO. : 5,705,721

DATED : January 6, 1998

INVENTOR(S) : Natu R. Patel

It is certified that error appears in the above-identified patent and that said Letters Patent is hereby corrected as shown below:

On the title page, item [73] Assignee, should read --Nalco/Exxon Energy Chemicals, L.P., Sugar Land, Texas--.

Signed and Sealed this

Twenty-first Day of April, 1998

*Attest:*

BRUCE LEHMAN

*Attesting Officer*   Commissioner of Patents and Trademarks